United States Patent [19]

Oda et al.

[11] Patent Number: 4,491,678

[45] Date of Patent: Jan. 1, 1985

[54] PROCESS FOR THE PRODUCTION OF PARA-XYLENE

[75] Inventors: Sumihiro Oda; Haruhito Sato, both of Sodegaura, Japan

[73] Assignee: Idemitsu Kosan Company Limited, Tokyo, Japan

[21] Appl. No.: 541,664

[22] Filed: Oct. 13, 1983

[30] Foreign Application Priority Data

| Oct. 19, 1982 | [JP] | Japan | 57-182206 |
| Dec. 10, 1982 | [JP] | Japan | 57-215511 |
| Mar. 28, 1983 | [JP] | Japan | 58-50460 |
| May 26, 1983 | [JP] | Japan | 58-91592 |
| May 27, 1983 | [JP] | Japan | 58-92510 |

[51] Int. Cl.$^3$ .............................. C07C 2/68
[52] U.S. Cl. ........................ 585/466; 585/467
[58] Field of Search .................... 585/466, 467

[56] References Cited

U.S. PATENT DOCUMENTS

| 3,965,210 | 6/1976 | Chu | 585/467 |
| 4,086,287 | 4/1978 | Kaeding et al. | 585/467 |
| 4,250,345 | 2/1981 | Chu | 585/466 |
| 4,276,437 | 6/1981 | Chu | 585/466 |
| 4,292,457 | 9/1981 | Klotz | 585/467 |
| 4,386,230 | 5/1983 | Hogan et al. | 585/467 |

*Primary Examiner*—Curtis R. Davis
*Attorney, Agent, or Firm*—Frishauf, Holtz, Goodman & Woodward

[57] ABSTRACT

A process for the production of para-xylene is described, comprising methylating benzene or toluene in the presence of a catalyst composed mainly of (A) crystalline borosilicate and (B) a compound containing at least one element selected from the group consisting of Group IIa elements of the Periodic Table, Group IIIa elements of the Periodic Table, silicon, and phosphorus. The process of the invention enables to produce paraxylene in a high selectivity and a high yield. Since the life of the catalyst as used herein is very long, the process of the invention can be performed continuously for long periods of time while maintaining its high catalytic activity.

17 Claims, 1 Drawing Figure

4,491,678

PROCESS FOR THE PRODUCTION OF PARA-XYLENE

FIELD OF THE INVENTION

The present invention relates to a process for the production of para-xylene, and more particularly, to a process for efficiently producing para-xylene by methylating benzene or toluene by the use of a specific catalyst.

BACKGROUND OF THE INVENTION

Various methods have been proposed for the production of para-xylene that is industrially very useful.

It is known that para-xylene is produced selectively when toluene is alkylated with methyl alcohol in the presence of a crystalline aluminosilicate catalyst containing fine pores having definite dimensions, such as ZSM-5 Zeolite.

It is also known that the selectivity of para-xylene is increased when sodium or hydrogen ions in the crystalline aluminosilicate catalyst are replaced by other metals. For example, Japanese patent application Laid-Open No. 7598/1980 discloses a process for the production of para-xylene from toluene and methyl alcohol and a process for the production of para-xylene by isomerization of ortho- or meta-xylene or disproportionation of toluene, using a catalyst comprising a siliceous support and a metal, such as chromium, beryllium, and titanium.

Conventional techniques, however, have disadvantages in that the selectivity of para-xylene is still insufficiently satisfactory and the catalytic activity drops in a relatively short period of time.

SUMMARY OF THE INVENTION

An object of the invention is to produce efficiently para-xylene from benzene or toluene.

Another object of the invention is to produce paraxylene in a very high selectivity.

Still another object of the invention is to maintain the activity of catalyst at a high level for a long period of time.

It has been found that the objects can be attained by using a catalyst composed mainly of (A) crystalline borosilicate and (B) a compound containing at least one element selected from the group consisting of Group IIa elements of the Periodic Table, Group IIIa elements of the Periodic Table, silicon, and phosphorus.

The present invention relates to a process for producing para-xylene by methylating benzene or toluene in the presence of a catalyst composed mainly of (A) crystalline borosilicate and (B) a compound containing at least one element selected from the group consisting of Group IIa elements of the Periodic Table, Group IIIa elements of the Periodic Table, silicon, and phosphorus.

DETAILED DESCRIPTION OF THE INVENTION

Figure 1:
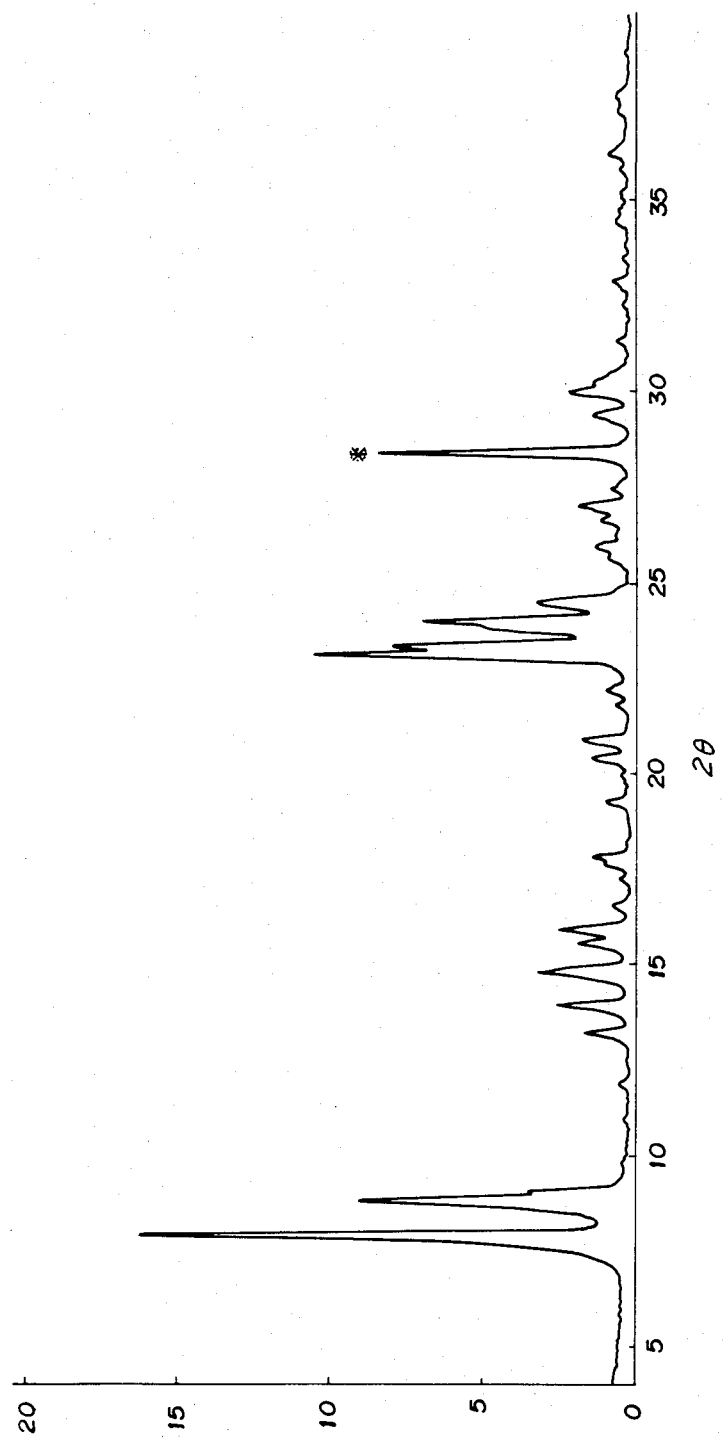
FIG. 1 shows an X-ray diffraction pattern of the crystalline borosilicate obtained in Referential Example as described hereinafter. In the figure, $\theta$ means the Bragg angle (degree). An asterisk (*) shows a peak of silicon oxide as a standard substance.

The catalyst as used herein contains Components (A) and (B) as described above as major ingredients.

As Component (A), crystalline borosilicate, various compounds can be used, including the crystalline borosilicates as described in, for example, Japanese patent application Laid-Open Nos. 55500/1978, 7598/1980, 84313/1981, 123817/1982, and 129820/1982.

These borosilicates can be prepared by various techniques. In general, they are prepared by adding a silica source, a boron source, and a crystallizing agent to an aqueous medium and subjecting the resulting mixture to a hydrothermal reaction. For example, ammonium type crystalline borosilicate is generally prepared as follows:

Solution A, an aqueous solution containing boric acid, concentrated sulfuric acid, and tetrapropylammonium bromide, Solution B, an aqueous solution of water glass (comprising silicon oxide, sodium oxide, and water), and Solution C, an aqueous solution of sodium chloride, are prepared separately. Solutions A and B were added dropwise to Solution C. The resulting mixture is, if necessary, adjusted in pH and heated in an autoclave. Then the mixture is cooled, washed, dried and calcined to prepare sodium type crystalline borosilicate. This sodium type crystalline borosilicate is further treated with an aqueous solution of ammonium nitrate to prepare ammonium type crystalline borosilicate. The thus-prepared borosilicate is in a powdery form; if desired, it can be molded by adding a binder such as alumina sol.

Component (B) of the catalyst as used herein is a compound containing at least one element selected from the group consisting of Group IIa elements of the Periodic Table, Group IIIa elements of the Periodic Table, silicon, and phosphorus. As Component (B), any compounds can be used as long as they contain at least one element as described above.

A typical example of Component (B) is silicon oxide. This silicon oxide may be deposited on or merely mixed with Component (A) of crystalline borosilicate.

A catalyst comprising crystalline borosilicate with silicon oxide deposited thereon can be prepared by various techniques. It is preferred to employ a method in which the crystalline borosilicate is impregnated with an organosilicon compound and, thereafter, calcined. As organosilicon compounds, various compounds can be used as long as they are converted into silicon oxide when calcined after impregnation. In general, organosilane, alkyl silicate, organosiloxane, and so forth are used. Of these compounds, tetraethyl silicate, diphenylsilicon, methylphenylsilicon, dimethylsilicon, and so forth are preferred. Particularly preferred are organosilicon compounds containing one silicon atom in the molecule, such as alkyl silicate, e.g., tetraethyl silicate and tetramethyl silicate, and organosilane, e.g., trimethylchlorosilane and dimethyldichlorosilane.

Various methods can be used to impregnate the crystalline borosilicate with the organosilicon compounds as described above. Usually the organosilicon compound is dissolved in an inactive organic solvent such as n-hexane and the crystalline borosilicate is soaked in the thus-prepared solution. The amount of the organosilicon compound used in the impregnation treatment is not critical; it can be determined appropriately depending on conditions. It is, as calculated as the amount of silicon oxide deposited, usually from 0.05 to 50 parts by weight, preferably from 0.1 to 25 parts by weight, and more preferably from 1 to 5 parts per 100 parts by weight of the crystalline borosilicate.

As described above, the crystalline borosilicate with silicon oxide deposited thereon can be prepared by impregnating the crystalline borosilicate with a predetermined amount of organosilicon compound and calcining the resulting mixture at a temperature of from about 550° to about 900° C. This is molded as such or, if necessary, after adding a binder such as alumina sol to form the desired catalyst.

Another example of Component (B) is a phosphorus compound. In the case of this phosphorus compound, it may be merely mixed with Component (A) of crystalline borosilicate. It is, however, preferred for the phosphorus compound to be deposited on the crystalline borosilicate. Phosphorus compounds which can be used include phosphoric acid; phosphates such as ammonium phosphate, sodium phosphate, and potassium phosphate; alkyl phosphates such as methyl phosphate, ethyl phosphate, propyl phosphate, and butyl phosphate; phosphorus oxychloride; phosphorus trichloride; phosphorus pentachloride; alkyl phosphite such as methyl phosphite and ethyl phosphite; metaphosphoric acid; pyrophosphoric acid; polyphosphoric acid; and hydrogenphosphate such as aluminum hydrogenphosphate, sodium hydrogenphosphate, potassium hydrogenphosphate, and ammonium hydrogenphosphate.

These phosphorus compounds can be deposited on the crystalline borosilicate by various techniques, such as a method in which the phosphorus compound and the crystalline borosilicate are mixed in a predetermined ratio, a method in which a crystalline borosilicate powder or mold is impregnated with a predetermined amount of solution of phosphorus compound, and a method in which after application of an ion exchange method as used in the preparation of modified zeolite, the resulting mass is calcined at a temperature of from 500° to 1,000° C. In a case in which a crystalline borosilicate powder is used, a phosphorus compound is deposited thereon and, thereafter, if desired, a binder such as alumina sol is added thereto. In this way, the final catalyst can be molded.

The amount of the phosphorus compound being deposited is not critical and can be determined appropriately. It is, as calculated as diphosphorus pentoxide ($P_2O_5$), usually from 0.1 to 40 parts by weight, preferably from 1 to 20 parts by weight, and more preferably from 2 to 10 parts by weight per 100 parts by weight of crystalline borosilicate.

It is effective to deposit a boron compound on the crystalline borosilicate in combination with the phosphorus compound as described above. Boron compounds which can be used include boric acid, ammonium borate, alkyl borate, metaboric acid, and tetraboric acid. In a case in which both the phosphorus compound and boron compound are deposited on the crystalline borosilicate, the amount of the phosphorus compound (calculated as diphosphorus pentoxide ($P_2O_5$)) being deposited is from 1 to 40 parts by weight, preferably from 2 to 20 parts by weight per 100 parts by weight of the crystalline borosilicate, and the amount of the boron compound (calculated as diboron trioxide ($B_2O_3$)) being deposited is from 1 to 40 parts by weight, preferably from 2 to 20 parts by weight per 100 parts by weight of the crystalline borosilicate.

Various techniques can be employed to deposit both the phosphorus compound and boron compound on the crystalline borosilicate. A preferred method involves depositing a boron compound on crystalline borosilicate by techniques such as impregnation and calcining the resulting mass, and subsequently further depositing a phosphorus compound thereon, for example, by impregnation and then calcining the resulting mass.

Another example of Component (B) is a compound of Group IIa metal, such as beryllium, magnesium, calcium, strontium or barium, of the Periodic Table. Of these compounds, magnesium or calcium compounds are preferred. Although there are a number of compounds containing Group IIa metals of the Periodic Table, those compounds are preferred which exist in the form of oxide in the final catalyst. Examples are various salts of the metals belonging to Group IIa of the Periodic Table, such as inorganic acid salts (e.g., nitric acid salts, sulfuric acid salts, and chlorides). Typical examples of such inorganic acid salts include calcium sulfate and magnesium nitrate. In addition, organic acid salts, such as calcium acetate, magnesium acetate, calcium formate, and magnesium formate, hydroxides, such as magnesium hydroxide and calcium hydroxide, and so forth can be used.

Although the compound of Group IIa metal of the Periodic Table may be merely mixed with the crystalline borosilicate, it is preferred to be deposited on the crystalline borosilicate. Another example of Component (B) is a compound of Group IIIa metal (e.g., boron, aluminum, gallium, indium or thallium) of the Periodic Table. Of these compounds, the compounds of boron, aluminum, and gallium are preferred. Those compounds are preferred which exist in the form of oxide in the final catalyst. For example, the salts or hydroxides of the metals belonging to Group IIIa of the Periodic Table can be used.

The compound of Group IIa or IIIa metal of the Periodic Table can be deposited on the crystalline borosilicate by various techniques. This deposition is usually achieved by impregnating the crystalline borosilicate with an aqueous solution of the compound as described above or by applying ion exchange. The ratio of the compound of Group IIa or IIIa metal of the Periodic Table to the crystalline borosilicate is not critical and can be determined appropriately taking into account various conditions. In general, the ratio of the metal compound (calculated as an oxide) to the crystalline borosilicate is from 0.05:100 to 50:100 (by weight) and preferably from 1:100 to 25:100 (by weight). The metal compound is introduced into the crystalline borosilicate by impregnation or ion exchange, for example, calcined, and if necessary, a binder such as alumina sol is added thereto. By molding the resulting mixture, the desired catalyst can be obtained.

It is effective to add the compound of Group IIa or IIIa metal of the Periodic Table as described, particularly a calcium compound, a magnesium compound or a gallium compound in combination with a boron compound or a phosphorus compound. Boron compounds which can be used include ammonium borate and alkyl borate as well as boric acid. As phosphorus compounds, the compounds as described above, for example, phosphoric acid and phosphate can be used.

In accordance with the process of the present invention, benzene or toluene is methylated by the use of a catalyst comprising Component (A) of crystalline borosilicate and Component (B) to produce para-xylene in a high selectivity. This methylation can be performed by either of a flow method and a batch method. In either case, para-xylene can be produced in a high selectivity and a high yield.

The starting material used in the present invention is benzene or toluene; in particular, toluene is preferred to use. In this methylation, a suitable methylating agent, such as methyl alcohol, dimethyl ether, methyl chloride, and methyl bromide, should be used. In particular, methyl alcohol and dimethyl ether are preferred.

Conditions for the methylation of benzene or toluene in the presence of the catalyst containing Components (A) and (B) as major ingredients can be determined appropriately depending on various situations. The reaction temperature is usually from 200° to 700° C. and preferably from 400° to 650° C.; the reaction pressure is usually from atmospheric pressure to 100 kilograms per square centimeter (by gauge) and preferably from atmospheric pressure to 10 kilograms per square centimeter (by gauge); the weight hourly space velocity (WHSV) is usually from 1 to 1,000 per hour, preferably from 1 to 200 per hour, and more preferably from 1 to 15 per hour; and the molar ratio of the starting material, benzene or toluene, to the methylating agent is usually from 1:5 to 20:1 and preferably from 1:1 to 10:1. When toluene and methyl alcohol are used as the starting material and methylating agent, respectively, the molar ratio of toluene to methyl alcohol is usually from 1:5 to 10:1 and preferably from 1:2 to 4:1. If the methylation reaction is performed in an atmosphere containing hydrogen gas, the activity of the catalyst can be maintained at a high level over a long period of time.

It is also effective that steam is introduced into the reaction system and the methylation reaction is performed in the presence of the steam. The amount of steam being introduced into the reaction system is not critical and can be determined appropriately taking into account various conditions. In general, the steam is introduced in an amount equimolar to or more than the methylating agent. In this case, it is preferred that the pressure of the steam to be introduced is slightly higher than the reaction pressure and the temperature of the steam is near the reaction temperature, since a variation in the pressure of the reaction system can be reduced. By performing the methylation reaction in the presence of steam, the service life of the catalyst used can be greatly increased.

The above-described effect resulting from the introduction of steam in the reaction system is remarkable particularly when a catalyst prepared using the compound of Group IIa metal of the Periodic Table as Component (B) is used. The reason is as follows: carbon precipitated on the catalyst during the methylation reaction undergoes a water gas reaction in combination with the steam. This water gas reaction is accelerated particularly by the compound of Group IIa metal of the Periodic Table. As a result, even if the methylation reaction is performed continuously for a long period of time, the deposition of carbon on the catalyst does not occur and the activity of the catalyst is maintained.

Some of the major advantages of the present invention are:

(1) para-xylene can be produced in a high selectivity and a high yield;

(2) the service life of the catalyst is very long; and (3) therefore, the methylation reaction can be performed continuously for a long period of time while maintaining a high catalytic activity.

Hence the process of the present invention is very useful as an industrial method of production of paraxylene and is of high practical value.

The present invention is described in greater detail with reference to the following Reference Example, Examples, and Comparative Example.

REFERENTIAL EXAMPLE

Preparation Crystalline Borosilicate

A mixture of 1.34 grams of boric acid, 17.68 grams of concentrated sulfuric acid, and 26.32 grams of tetrapropylammonium bromide was dissolved in 250 milliliters of water to prepare a solution, Solution A. Separately 211.1 grams of water glass (consisting of 28.95% by weight of silicon oxide, 9.40% by weight of sodium oxide, and 61.65% by weight of water) was dissolved in 250 milliliters of water to prepare a solution, Solution B. Then Solutions A and B were simultaneously dropped into a solution prepared by dissolving 79.0 grams of sodium chloride in 122 milliliters of water, at room temperature over 10 minutes. The resulting mixture was adjusted to pH 9.5 with sulfuric acid. The mixture was then placed in an autoclave and heated at a temperature of 170° C. for 20 hours. The contents of the autoclave were filtered while cooling, and the solids thus obtained were washed and dried at 120° C. for 6 hours. The solids were further calcined at 550° C. for 8 hours to form 50 grams of Sodium type crystalline borosilicate. The weight ratio of $SiO_2$ to $B_2O_3$ in the sodium type crystalline borosilicate was 100:1. The X-ray diffraction pattern of the sodium type crystalline borosilicate is as shown in FIG. 1.

Then 30 grams of sodium type crystalline borosilicate as prepared above was added to a five-fold (by weight) amount of a 1 normal aqueous solution of ammonium nitrate, and heated under reflux for 8 hours. At the end of the time, the mixture was cooled and allowed to stand, and the supernatant liquid was removed by decantation. This reflux-decantation process was repeated three times. The contents were then filtered, washed, and dried at 120° C. for 10 hours to obtain 29.5 grams of ammonium type crystalline borosilicate. Part of the crystalline borosilicate was calcined at 550° C. for 6 hours to form proton type crystalline borosilicate.

EXAMPLE 1

(1) Preparation of Catalyst

In a solution prepared by dissolving 1.2 grams of silicon (trade name: KF-54, produced by Shinetsu Kagaku Co., Ltd.; viscosity: 400 centistokes (25° C.); major ingredient: diphenylsilicon) in 100 milliters of n-hexane was soaked 5 grams of ammonium type borosilicate as prepared in the foregoing Referential Example at room temperature for 24 hours. Then the borosilicate was evaporated to dryness, dried at 120° C. for 10 hours, and further calcined at 600° C. for 5 hours.

An alumina sol binder was added to the powder as prepared above so that the binder content was 20% by weight, and the resulting mixture was molded, dried at 120° C. for 5 hours, and further calcined at 600° C. for 4 hours to form a catalyst.

(2) Production of Para-Xylene

An atmospheric pressure fixed-bed flow type reaction tube was charged with 2 grams of the catalyst as prepared in (1) above. While maintaining the reaction temperature at 600° C., a 4:1 (by mole) mixture of toluene and methyl alcohol was introduced in the reaction tube at a weight hourly space velocity (WHSV) of 9.2 per hour and reacted for 3 hours. The results are shown in Table 1.

EXAMPLE 2

(1) Preparation of Catalyst

A catalyst was prepared in the same manner as in Example 1 (1) except that silicone (trade name: SH-710, produced by Toray Silicone Co., Ltd.; viscosity: 475–525 centistokes (25° C.); major ingredient: methylphenylsilicone) was used.

(2) Production of Para-Xylene

The procedure of Example 1 (2) was repeated wherein the catalyst as prepared in (1) above was used. The results are shown in Table 1.

EXAMPLE 3

(1) Preparation of Catalyst

A catalyst was prepared in the same manner as in Example 1 (1) except that silicone (trade name: SH-200, produced by Toray Silicone Co., Ltd.; viscosity: 100 centistokes (25° C.); major ingredient: dimethylsilicone) was used.

(2) Production of Para-Xylene

The procedure of Example 1 (2) was repeated wherein the catalyst as prepared in (1) above was used. The results are shown in Table 1.

EXAMPLE 4

(1) Preparation of Catalyst

Nine grams of the proton type borosilicate as prepared in the foregoing Referential Example was added to 50 grams of tetraethyl ortho silicate, and the resulting mixture was heated under reflux for 8 hours. The contents were filtered, and the residue was washed with n-hexane, dried at 120° C. for 8 hours and further calcined at 550° C. for 6 hours.

An alumina sol binder was added to the powder as prepared above so that the binder content was 20% by weight, and the resulting mixture was then molded. This mold was then dried at 120° C. for 5 hours and calcined at 600° C. for 4 hours and further at 900° C. for 3 hours to form the desired catalyst.

(2) Production of Para-Xylene

The procedure of Example 1 (2) was repeated wherein the catalyst as prepared in (1) above was used. The results are shown in Table 1.

EXAMPLE 5

(1) Preparation of Catalyst

In a solution prepared by dissolving 0.88 gram of tetra ethyl orthosilicate in 60 milliliters of n-hexane was soaked 5 grams of the ammonium type borosilicate as prepared in the foregoing Referential Example at room temperature for 24 hours. Then the mixture was evaporated to dryness, and the residue was dried at 120° C. for 10 hours, and further calcined at 600° C. for 5 hours. Then 5 grams of the powder thus obtained was added to a solution prepared by dissolving 1.2 grams of silicone (trade name: SH-200, produced by Roray Silicone Co., Ltd.; viscosity: 100 centistokes (25° C.); major ingredient: dimethylsilicone) in 100 milliliters of n-hexane and soaked therein at room temperature for 24 hours. The mixture was then evaporated to dryness, and the residue was dried at 120° C. for 10 hours and further calcined at 600° C. for 5 hours. An alumina sol binder was added to the powder thus obtained so that the binder content was 20% by weight, and the resulting mixture was then molded. This mold was dried at 120° C. for 5 hours and thereafter calcined at 600° C. for 4 hours to form the desired catalyst.

(2) Production of Para-Xylene

The procedure of Example 1 (2) was repeated wherein the catalyst as prepared in (1) above was used. The results are shown in Table 1.

EXAMPLE 6

(1) Preparation of Catalyst

Two grams of trimethylchlorosilane was dissolved in 100 milliliters of benzene. Then 5 grams of the proton type borosilicate as prepared in the foregoing Referential Example was added to the solution as prepared above and stirred at room temperature for 8 hours. The solids were filtered off, washed with benzene, dried at 120° C. for 16 hours, and calcined at 550° C. for 5 hours. An alumina sol binder was added to the powder this obtained so that the binder content was 20% by weight. The resulting mixture was molded, dried at 120° C. for 5 hours, and calcined at 550° C. for 6 hours and further at 900° C. for 2 hours to form the desired catalyst.

(2) Production of Para-Xylene

An atmospheric pressure fixed-bed flow type reaction tube was charged with 2 grams of the catalyst as prepared in (1) above. A 2:1 (by mole) mixture of toluene and methyl alcohol was introduced in the reaction tube and reacted at 600° C. and WHSV=9.2 per hour. The results as measured after 4 hours from the start of the reaction are shown in Table 1.

EXAMPLE 7

(1) Preparation of Catalyst

Five grams of the proton type borosilicate as prepared in the foregoing Referential Example was added to a solution prepared by dissolving 0.88 gram of tetra ethyl orthosilicate in 60 milliliters of n-hexane. The resulting mixture was refluxed for 10 hours and then evaporated to dryness. The residue thus obtained was dried at 120° C. for 16 hours and calcined at 550° C. for 6 hours. Then it was molded in the same manner as in Example 6 (1) to form the desired catalyst.

(2) Production of Para-Xylene

The procedure of Example 6 (2) was repeated wherein the catalyst as prepared in (1) above was used. The results are shown in Table 1.

EXAMPLE 8

The procedure of Example 6 (2) was repeated wherein the catalyst as prepared in Example 7 (1) was used and a 4:1 (by mole) mixture of toluene and methyl alcohol was introduced. The results are shown in Table 1.

COMPARATIVE EXAMPLE 1

(1) Preparation of Catalyst

An alumina sol binder was added to the ammonium type borosilicate powder as prepared in the foregoing Referential Example so that the binder content was 20% by weight. The resulting mixture was molded, dried at 120° C. for 4 hours, and calcined at 550° C. for 6 hours.

(2) Production of Para-Xylene

The procedure of Example 1 (2) was repeated wherein the catalyst as prepared in (1) above was used. The results are shown in Table 1.

TABLE 1

| Run No. | Conversion of Toluene (%) | $\dfrac{\text{Total Xylene}}{\text{Aromatic Fraction Formed}} \times 100\ (\%)$ | $\dfrac{\text{P-Xylene}}{\text{Total Xylene}} \times 100\ (\%)$ |
| --- | --- | --- | --- |
| Example 1 | 20 | 95 | 82 |
| Example 2 | 19 | 95 | 81 |
| Example 3 | 20 | 95 | 66 |
| Example 4 | 23 | 94 | 79 |
| Example 5 | 17 | 95 | 86 |
| Example 6 | 31 | 95 | 91 |
| Example 7 | 31 | 96 | 97 |
| Example 8 | 17 | 95 | 90 |
| Comparative Example 1 | 21 | 93 | 48 |

EXAMPLE 9

(1) Preparation of Catalyst

To a solution prepared by dissolving 2.66 grams of phosphoric acid (concentration: 85%) in 50 milliliters of water was added 10 grams of the ammonium type crystalline borosilicate as prepared in the foregoing Referential Example, and the resulting mixture was maintained at 90° C. for 16 hours and then evaporated to dryness. The thus-obtained powder was drided at 120° C. for 16 hours and then calcined at 550° C. for 6 hours. An alumina sol binder was added to the above-calcined powder so that the alumina content after calcination was 20% by weight, and the resulting mixture was molded, dried at 120° C. for 6 hours, and calcined at 550° C. for 6 hours to form the desired catalyst.

(2) Production of Para-Xylene

An atmospheric pressure fixed-bed flow type reaction tube was charged with 2 grams of the catalyst as prepared in Example 9 (1). While maintaining the reaction temperature at 600° C., a 4:1 (by mole) mixture of toluene and methyl alcohol was introduced into the reaction tube at a weight hourly space velocity (WHSV) of 9.2 per hour and reacted for 3 hours. The results are shown in Table 2.

EXAMPLE 10

(1) Preparation of Catalyst

Fifteen grams of the proton type crystalline borosilicate as prepared in the foregoing Referential Example was placed in a three-necked flask, heated at 200° C. for 4 hours in an argon gas atmosphere, and then cooled to room temperature. Then 100 grams of trimethyl phosphite was placed in the flask and heated under reflux at 112° C. for 20 hours in an argon gas atmosphere. The mixture was cooled and filtered, and the residue thus obtained was washed with dichloromethane and n-pentane, dried at 120° C. for 6 hours, and calcined at 550° C. for 6 hours.

An alumina sol binder was added to the calcined powder as obtained above so that the alumina content after calcination was 20% by weight. The resulting mixture was molded, dried at 120° C. for 6 hours, and calcined at 550° C. for 6 hours and further at 900° C. for 2 hours to form the desired catalyst.

(2) Production of Para-Xylene

The procedure of Example 9 (2) was repeated wherein the catalyst as prepared in Example 10 (1) was used. The results are shown in Table 2.

EXAMPLE 11

(1) Preparation of Catalyst

To a solution prepared by dissolving 0.51 grams of magnesium nitrate in 50 milliliters of water was added 2.5 grams of the catalyst as prepared in Example 10 (1), and the resulting mixture was maintained at 90° C. for 25 hours and filtered. The residue was washed, dried at 120° C. for 8 hours, and calcined at 550° C. for 6 hours to form the desired catalyst.

(2) Production of Para-Xylene

The procedure of Example 9 (2) was repeated wherein the catalyst as prepared in (1) above was used. The results are shown in Table 2.

EXAMPLE 12

(1) Preparation of Catalyst

To a solution prepared by dissolving 0.47 gram of calcium nitrate in 20 milliliters of water was added 2.3 grams of the catalyst as prepared in Example 10 (1), and the resulting mixture was maintained at 90° C. for 24 hours and filtered. The residue thus obtained was washed, dried at 120° C. for 8 hours, and calcined at 550° C. for 6 hours to form the desired catalyst.

(2) Production of Para-Xylene

The procedure of Example 9 (2) was repeated wherein the catalyst as prepared in (1) above was used. The results are shown in Table 2.

EXAMPLE 13

(1) Preparation of Catalyst

Seven grams of the ammonium type crystalline borosilicate as prepared in the foregoing Referential Example was added to a solution prepared by dissolving 0.65 gram of boric acid in 30 milliliters of water. The resulting mixture was maintained at 90° C. for 16 hours and then evaporated to dryness. The thus-obtained residue was dried at 120° C. for 10 hours and further calcined at 550° C. for 5 hours. Then 3 grams of the powder as prepared above was added to a solution prepared by dissolving 0.44 gram of phosphoric acid in 20 milliliters of water. The resulting mixture was maintained at 90° C. for 16 hours and then evaporated to dryness. The residue thus obtained was dried at 120° C. for 10 hours and further calcined at 550° C. for 5 hours. An alumina sol binder was added to the above-calcined residue so that the alumina content after calcination was 20% by weight, and the resulting mixture was molded, dried at 120° C. for 14 hours, and calcined at 550° C. for 6 hours to form a catalyst in which $P_2O_5$ and $B_2O_3$ contents were 8.3% by weight and 5.0% by weight, respectively, based on the crystalline borosilicate.

(2) Production of Para-Xylene

An atmospheric pressure fixed-bed flow type reaction tube was charged with 2 grams of the catalyst as prepared in (1) above. While maintaining the reaction temperature at 600° C., a 4:1 (by mole) mixture of toluene and methyl alcohol was introduced into the reaction tube at a weight hourly space velocity (WHSV) of 9.2 per hour and reacted for 3 hours. The results are shown in Table 2.

TABLE 2

| Run No. | Conversion of Toluene (%) | $\dfrac{\text{Total Xylene Formed}}{\text{Aromatic Fraction Formed}} \times 100\,(\%)$ | $\dfrac{\text{P-Xylene}}{\text{Total Xylene}} \times 100\,(\%)$ |
|---|---|---|---|
| Example 9 | 7 | 91 | 89 |
| Example 10 | 20 | 96 | 85 |
| Example 11 | 20 | 97 | 93 |
| Example 12 | 19 | 97 | 89 |
| Example 13 | 20 | 94 | 84 |

EXAMPLE 14

(1) Preparation of Catalyst

Eight grams of the ammonium type crystalline borosilicate as prepared in the foregoing Referential Example was added to a solution prepared by dissolving 3.76 grams of calcium nitrate in 80 milliliters of water and soaked therein at 90° C. for 16 hours to conduct impregnation treatment. The mixture was then evaporated to dryness, and the residue thus obtained was dried at 120° C. for 8 hours and further calcined at 550° C. for 6 hours. To the thus-obtained powder was added an alumina sol binder so that the binder content was 20% by weight. The resulting mixture was molded, dried at 120° C. for 5 hours, and further calcined at 550° C. for 4 hours to form a catalyst consisting of calcium oxide and crystalline borosilicate.

(2) Production of Para-Xylene

An atmospheric pressure fixed-bed flow type reaction tube was charged with 2 grams of the catalyst as prepared in (1) above. While maintaining the reaction temperature at 600° C., a 4:1 (by mole) mixture of toluene and methyl alcohol was introduced into the reaction tube at a weight hourly space velocity (WHSV) of 9.2 per hour and reacted for 3 hours. The results are shown in Table 3.

EXAMPLE 15

(1) Preparation of Catalyst

A catalyst was prepared in the same manner as in Example 14 (1) except that the final calcination was performed at 900° C. for 3 hours.

(2) Production of Para-Xylene

The procedure of Example 14 (2) was repeated wherein the catalyst as prepared above was used. The results are shown in Table 3.

EXAMPLE 16

(1) Preparation of Catalyst

Eight grams of the ammonium type crystalline borosilicate as prepared in the foregoing Referential Example was added to a solution prepared by dissolving 4.1 grams of magnesium nitrate in 80 milliliters of water and soaked therein at 90° C. for 14 hours to conduct impregnation treatment. Then solids were filtered off, washed, dried at 120° C. for 8 hours, and further calcined at 550° C. for 6 hours. The thus-obtained powder was molded and calcined in the same manner as in Example 15 (1) to form a catalyst comprising magnesium oxide and crystalline borosilicate.

(2) Production of Para-Xylene

The procedure of Example 14 (2) was repeated wherein the catalyst as prepared in (1) above was used. The results are shown in Table 3.

EXAMPLE 17

(1) Preparation of Catalyst

Ten grams of the ammonium type crystalline borosilicate as prepared in the foregoing Referential Example was added to a solution prepared by dissolving 1.97 grams of boric acid in 50 milliliters of water and soaked therein at 90° C. for 20 hours to conduct impregnation treatment. The mixture was evaporated to dryness, and the residue thus obtained was dried at 120° C. for 7 hours and calcined at 550° C. for 8 hours. Then 2.8 grams of the powder as prepared above was impregnated with 50 milliliters of an aqueous solution with 1.98 grams of magnesium nitrate dissolved therein and heated at 90° C. for 14 hours. The mixture was then evaporated to dryness, and the residue was dried at 120° C. for 13 hours and calcined at 550° C. for 8 hours. To the thus-prepared powder was added an alumina sol binder so that the binder content was 20% by weight. The mixture was then molded, dried at 120° C. for 5 hours, and further calcined at 550° C. for 5 hours to form a catalyst comprising magnesium oxide, boron oxide and crystalline borosilicate.

(2) Production of Para-Xylene

The procedure of Example 14 (2) was repeated wherein the catalyst as prepared in (1) above was used. The results are shown in Table 3.

TABLE 3

| Run No. | Conversion of Toluene (%) | $\dfrac{\text{Total Xylene}}{\text{Aromatic Fraction Formed}} \times 100\,(\%)$ | $\dfrac{\text{P-Xylene}}{\text{Total Xylene}} \times 100\,(\%)$ |
|---|---|---|---|
| Example 14 | 20 | 92 | 68 |
| Example 15 | 21 | 96 | 94 |
| Example 16 | 16 | 96 | 92 |
| Example 17 | 15 | 92 | 57 |

EXAMPLE 18

Production of Para-Xylene

An atmospheric pressure fixed-bed flow type reaction tube was charged with 5 grams of the catalyst, as prepared in Example 15 (1). Toluene and methyl alcohol were introduced into the reaction tube at a molar ratio of toluene: methyl alcohol=4:1 under the conditions of temperature of 600° C. and a weight hourly space velocity (WHSV) of 2 per hour, and simultaneously steam was introduced into the reaction tube in an amount equal to the total mole number of the toluene and methyl alcohol to perform a methylation reaction. The results as measured after 20 hours and also 80 hours from the start of the reaction are shown in Table 4.

EXAMPLE 19

(1) Preparation of Catalyst

Five grams of the ammonium type crystalline borosilicate as prepared in the foregoing Referential Example was added to a solution prepared by dissolving 15 grams of magnesium acetate in 10 milliliters of water and soaked therein at 90° C. for 8 hours. The solids were filtered off and washed. Then, after evaporation to dryness, the same treatment as in Example 15 (1) was applied to form a catalyst.

(2) Production of Para-Xylene

The procedure of Example 18 was repeated wherein the catalyst as prepared in (1) above was used. The results are shown in Table 4.

TABLE 4

| Run No. | Reaction Time (hours) | Conversion of Toluene (%) | $\frac{\text{Total Xylene}}{\text{Aromatic Fraction Formed}} \times 100\,(\%)$ | $\frac{\text{P-Xylene}}{\text{Total Xylene}} \times 100\,(\%)$ |
|---|---|---|---|---|
| Example 18 | 20 | 22 | 95 | 90 |
|  | 80 | 22 | 96 | 92 |
| Example 19 | 20 | 19 | 93 | 92 |
|  | 80 | 18 | 94 | 93 |

EXAMPLE 20

(1) Preparation of Catalyst

Twenty grams of the ammonium type crystalline borosilicate as prepared in the foregoing Referential Example was added to a solution prepared by dissolving 1.87 grams of boric acid in 80 milliliters of water and stirred at 90° C. for 16 hours. Then the mixture was evaporated to dryness, and the residue was dried at 120° C. for 16 hours and calcined at 550° C. for 6 hours. To the thus-obtained calcined powder was added an alumina sol binder so that the binder content was 20% by weight, and the resulting mixture was molded in a granular form, dried at 120° C. for 5 hours, and calcined at 550° C. for 4 hours to form a catalyst.

(2) Production of Para-Xylene

An atmospheric pressure fixed-bed flow type reaction tube was charged with 2 grams of the catalyst as prepared in (1) above. While maintaining the reaction temperature at 600° C., toluene and methyl alcohol were introduced into the reaction tube in a molar ratio of toluene: methyl alcohol=4:1 at a weight hourly space velocity (WHSV) of 9.2 per hour and reacted. The results as measured after 3 hours from the start of the reaction are shown in Table 5.

EXAMPLE 21

(1) Preparation of Catalyst

Ten grams of the ammonium type crystalline borosilicate as prepared in the foregoing Referential Example was added to a solution prepared by dissolving 3.87 grams of aluminum nitrate in 60 milliliters of methyl alcohol and stirred at 65° C. for 5 hours. Thereafter the same preparation as in Example 20 (1) was applied to form a catalyst.

(2) Production of Para-Xylene

The procedure of Example 20 (2) was repeated wherein the catalyst as prepared in (1) above was used. The results as measured after 3 hours from the start of the reaction are shown in Table 5.

EXAMPLE 22

(1) Preparation of Catalyst

Five grams of the ammonium type crystalline borosilicate as prepared in the foregoing Referential Example was added to a solution prepared by dissolving 0.82 gram of gallium nitrate in 50 milliliters of water and stirred at 90° C. for 5 hours. Thereafter the same preparation as in Example 20 (1) was applied to form a catalyst.

(2) Production of Para-Xylene

The procedure of Example 20 (2) was repeated wherein the catalyst as prepared in (1) above was used. The results as measured after 3 hours from the start of the reaction are shown in Table 5.

EXAMPLE 23

(1) Preparation of Catalyst

Five grams of the catalyst powder as prepared in Example 22 was added to a 10% by weight aqueous solution of phosphoric acid and stirred at 90° C. for 16 hours. Thereafter the same preparation as in Example 20 (1) was applied to form a catalyst.

(2) Production of Para-Xylene

The procedure of Example 20 (2) was repeated wherein the catalyst as prepared in (1) above was used. The results as measured after 3 hours from the start of the reaction are shown in Table 5.

TABLE 5

| Run No. | Conversion of Toluene (%) | $\frac{\text{Total Xylene}}{\text{Aromatic Fraction Formed}} \times 100\,(\%)$ | $\frac{\text{Para-Xylene}}{\text{Total Xylene}} \times 100\,(\%)$ |
|---|---|---|---|
| Example 20 | 20 | 97 | 82 |
| Example 21 | 21 | 94 | 74 |
| Example 22 | 22 | 92 | 69 |
| Example 23 | 20 | 96 | 82 |

What is claimed is:

1. A process for producing para-xylene comprising reacting benzene or toluene and a methylating agent in the presence of a catalyst comprising (A) crystalline borosilicate and (B) a compound containing at least one element selected from the group consisting of Group IIa elements of the Periodic Table, Group IIIa elements of the Periodic Table, silicon, and phosphorus.

2. The process as claimed in claim 1, wherein the catalyst comprises crystalline borosilicate and silicon oxide deposited thereon.

3. The process as claimed in claim 1 or 2, wherein the catalyst is prepared by impregnating the crystalline borosilicate with an organosilicon compound and calcining the resulting mixture.

4. The process as claimed in claim 3, wherein the amount of the organosilicon compound used in the impregnation is from 0.05 to 50 parts by weight (calculated as silicon oxide) per 100 parts by weight of the crystalline borosilicate.

5. The process as claimed in claim 3, wherein the organosilicon compound is an organosilane, an alkyl silicate or an organosiloxane.

6. The process as claimed in claim 1, wherein the catalyst comprises crystalline borosilicate and a phosphorus compound deposited thereon.

7. The process as claimed in claim 6, wherein the amount of the phosphorus compound deposited was from 0.1 to 40 parts by weight (calculated as diphosphorus pentoxide) per 100 parts by weight of the crystalline borosilicate.

8. The process as claimed in claim 1, wherein the catalyst comprises crystalline borosilicate, and a phosphorus compound and a boron compound deposited thereon.

9. The process as claimed in claim 8, wherein the amounts of the phosphorus compound and the boron compound being deposited are from 1 to 40 parts by weight (calculated as diphosphorus pentoxide) and from 1 to 40 parts by weight (calculated as diboron trioxide), respectively, per 100 parts by weight of the crystalline borosilicate.

10. The process as claimed in claim 1, wherein the catalyst comprises crystalline borosilicate and a calcium compound or a magnesium compound deposited thereon.

11. The process as claimed in claim 1, wherein the catalyst comprises crystalline borosilicate, and a calcium or magnesium compound and a boron compound deposited thereon.

12. The process as claimed in claim 1, wherein the catalyst comprises crystalline borosilicate, and a calcium or magnesium compound and a phosphorus compound deposited thereon.

13. The process as claimed in claim 1, wherein the catalyst comprises crystalline borosilicate, and an aluminum compound or a gallium compound deposited thereon.

14. The process as claimed in claim 1, wherein the catalyst comprises crystalline borosilicate, and a gallium compound and a phosphorus compound deposited thereon.

15. The process as claimed in claim 1, wherein the methylation reaction of benzene or toluene is performed in the presence of steam.

16. The process as claimed in claim 1, wherein the methylating agent is methyl alcohol or dimethyl ether.

17. The process as claimed in claim 4, wherein the an organosilicon compound is organosilane, an alkyl silicate or an organosiloxane.

* * * * *